United States Patent
Clark et al.

(10) Patent No.: US 9,693,854 B2
(45) Date of Patent: Jul. 4, 2017

(54) DEVICES FOR FORMING COLLATERAL CHANNELS AND RELATED METHODS OF USE

(71) Applicant: Boston Scientific Scimed, Inc., Maple Grove, MN (US)

(72) Inventors: Bryan Allen Clark, Forest Lake, MN (US); Aiden Flanagan, Kilcolgan (IE); Brian L. Schmidt, White Bear Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 147 days.

(21) Appl. No.: 14/672,862

(22) Filed: Mar. 30, 2015

(65) Prior Publication Data

US 2015/0272718 A1    Oct. 1, 2015

Related U.S. Application Data (60) Provisional application No. 61/972,640, filed on Mar. 31, 2014.

(51) Int. Cl.
*A61F 2/04*    (2013.01)

(52) U.S. Cl.
CPC .......... *A61F 2/04* (2013.01); *A61F 2002/043* (2013.01); *A61F 2210/0004* (2013.01); *A61F 2250/0071* (2013.01)

(58) Field of Classification Search
CPC ...... A61F 2/04; A61F 2002/043; A61B 17/34; A61M 16/00
See application file for complete search history.

(56) References Cited

U.S. PATENT DOCUMENTS

| | | | |
|---|---|---|---|
| 7,883,471 B2 | 2/2011 | Aljuri et al. | |
| 2004/0073201 A1* | 4/2004 | Cooper | A61B 8/12 606/14 |
| 2004/0244802 A1* | 12/2004 | Tanaka | A61M 16/04 128/207.16 |
| 2008/0183275 A1* | 7/2008 | Schmid | A61F 2/844 623/1.15 |
| 2009/0076491 A1 | 3/2009 | Roschak et al. | |
| 2009/0205645 A1* | 8/2009 | Tanaka | A61K 9/007 128/200.24 |
| 2013/0172921 A1* | 7/2013 | Kinoshita | A61B 17/34 606/185 |

OTHER PUBLICATIONS

Van Allen et al., "Gaseous Interchange Between Adjacent Lung Lobules", 1930, pp. 297-300, vol. 2, Yale Journal of Biology and Medicine (5 pages).

(Continued)

*Primary Examiner* — Katrina Stransky
*Assistant Examiner* — Daniel Bissing
(74) *Attorney, Agent, or Firm* — Bookoff McAndrews, PLLC (57) ABSTRACT

A method for treating a lung may include forming a channel between a first airway and a second airway through a tissue of the lung to allow air trapped within the first airway to flow through the channel and the second airway, and inserting a support member into the channel.

16 Claims, 6 Drawing Sheets

(56) References Cited

OTHER PUBLICATIONS

Hogg et al., "The Resistance of Collateral Channels in Excised Human Lungs", 1969, pp. 421-431, vol. 48, The Journal of Clinical Investigation (11 pages).
Terry et al., "Collateral Ventilation in Man", Jan. 5, 1978, pp. 10-15, vol. 298, No. 1, The New England Journal of Medicine (6 pages).
Macklem, Peter T., "Collateral Ventilation", Jan. 5, 1978, pp. 49-50, vol. 298, No. 1, The New England Journal of Medicine (2 pages).

* cited by examiner

DEVICES FOR FORMING COLLATERAL CHANNELS AND RELATED METHODS OF USE

CROSS-REFERENCE TO RELATED APPLICATION

This patent application claims the benefit of priority to U.S. Provisional Patent Application No. 61/972,640, filed Mar. 31, 2014, the entirety of which is incorporated herein by reference.

TECHNICAL FIELD

Embodiments of the present disclosure relate to devices for forming collateral channels in, for example, a lung, and related methods of implantation and use.

BACKGROUND

Chronic obstructive pulmonary disease (COPD) includes conditions such as, e.g., chronic bronchitis and emphysema. COPD currently affects over 15 million people in the United States alone and is currently the third leading cause of death in the country. The primary cause of COPD is the inhalation of cigarette smoke, responsible for over 90% of COPD cases. The economic and social burden of the disease is substantial and is increasing.

Chronic bronchitis is characterized by chronic cough with sputum production. Due to airway inflammation, mucus hypersecretion, airway hyperresponsiveness, and eventual fibrosis of the airway walls, significant airflow and gas exchange limitations result.

Emphysema is characterized by the destruction of the lung parenchyma. This destruction of the lung parenchyma leads to a loss of elastic recoil and tethering that maintains airway patency. Because bronchioles are not supported by cartilage like the larger airways, they have little intrinsic support and therefore are susceptible to collapse when destruction of tethering occurs, particularly during exhalation.

Inhaled cigarette smoke (and other noxious gases such as biomass smoke) cause lung inflammation, and this inflammatory response in COPD patients may lead to destruction of the lung parenchyma, emphysema, disruption of normal repair and defense mechanisms, and small airway fibrosis. Several pathological changes occur that can result in the narrowing of the airway lumen and the loss of the tethering function of the lung parenchyma, promoting a reduction of expiratory flow. These pathological changes include an inflammatory cell infiltrate, goblet-cell metaplasia, squamous-cell metaplasia, fibrosis, and an increased smooth-muscle mass.

One major symptom of COPD is reduced lung function, which is measured by Forced Expiratory Volume (FEV1). FEV1 defines the maximum volume of air that a person can forcibly breathe out in one second. FEV1 progressively decreases in COPD patients. COPD causes contraction, inflammation, and remodelling of the airways, increasing airflow resistance and lowering FEV1. Increased airflow resistance is particularly prevalent in the small airways (e.g., in airways having a diameter of 2 mm or less). Another complicating factor in COPD patients is excessive mucus secretion that can easily block an already small or narrow airway. In healthy individuals, there is no significant airflow limitation.

Hyperinflation is a clinical symptom of emphysema caused by air trapping whereby air can easily enter the parenchyma but becomes trapped by closing airways during exhalation. Emphysematic bula or voids can become permanently inflated causing remodelling of the chest, and a subsequent 'barrel chested' appearance. Also, during exercise, the inability to exhale rapidly causes dynamic hyperinflation that eases only by resting and by patients using a 'pursed lip' technique to deflate their lungs. This hyperinflation symptom causes extreme stress and anxiety to COPD patients.

Some bronchi and bronchioles may be partially or totally occluded by mucus plugs. The inflammatory changes in small airways may include acute inflammation and fibrosis. The changes in the diseased small airways are associated with two distinct components—one potentially reversible and the other irreversible. The potentially reversible component is related to mucus plugging, acute inflammation, and increased muscle tone due to hyper-responsivity. The irreversible component is related to fibrosis, distortion, narrowing due to tissue (e.g., muscle) thickening, and obliteration of small airways representing fixed obstruction in patients with COPD.

Many patients with COPD have a combination of small airways disease and emphysema. Studies have shown that the lower or dependent lung has a bigger impact on lung function and patients symptom than the upper lung. This is because emphysema is more severe in the upper lung, the relative size of each part of the lung, and the relative amount of respiration taking place in each part of the lung.

Collateral ventilation is the ability of gas to move from one part of the lung to another through nonanatomic pathways. The importance of collateral ventilation is minimal in normal, healthy lungs, because the resistance to air flow is higher in collateral channels than in the airways. However, the resistance of air flow in collateral channels is relatively low in patients with emphysema. In emphysematous lungs, collateral ventilation may provide important channels for gas distribution and may be therapeutically useful. In emphysema, the loss of tethering of the bronchioles in the lung parenchyma results in collapse on exhalation, which causes trapping of air and hyperinflation. The creation of direct passages between emphysematous pulmonary parenchyma and bronchial airways (airway bypass) may improve expiratory flow and volume and reduce hyperinflation.

In small airways disease, the narrowing and obliteration of the airways closes off access to distal healthy alveoli. However, these healthy alveoli do not undergo atelectasis, and thus, are likely being ventilated by collateral ventilation through the Pores of Kohn. Unfortunately, this ventilation is not adequate for respiration and $CO_2$ can build up in the alveoli.

Thus, there remains a need for improved methods and devices that allow for better treatment of COPD patients. It may therefore be beneficial to provide techniques to treat the damaged lung system such that the more air can be transferred to and from the alveoli (for gas transfer) and increase FEV1.

SUMMARY

Embodiments of the present disclosure relate to devices for forming collateral channels, in, for example, a lung, and related methods of implantation and use.

In one aspect, the present disclosure is directed to a method for treating a lung. The method may include forming a channel between a first airway and a second airway through a tissue of the lung to allow air trapped within the first airway to flow through the channel and the second airway, and inserting a support member into the channel.

Various examples of the present disclosure may include one or more of the following aspects: wherein the tissue of the lung include a parenchymal tissue of the lung; wherein the channel extends through a third airway wherein the tissue of the lung includes alveoli; wherein the channel is partially disposed outside of the lung; wherein the channel is disposed through the pleural cavity; wherein the first airway is disposed in a first lobe of a patient and the second airway is disposed in a second lobe of the patient; wherein the support member further includes a material to prevent cell ingrowth into the channel; wherein the support member is biodegradable; wherein the support member includes an outer member that is permeable to gases and impermeable to liquids; wherein the support member is a spiral member, a tubular member, or a stent-shaped member; wherein the tubular member includes a plurality of pores; wherein the support member is inserted via a bronchoscopic member, and wherein the support member remains in the channel after the bronchoscopic member has been removed from the lung system; wherein the support member is coupled to the distal end of the bronchoscopic member by a frangible link; wherein the support member is positioned into the channel by the bronchoscopic member, and the frangible link is severed to secure the support member within the channel; wherein the support member is axially elastic; wherein the support member further includes a time-releasable drug that is a bronchodilator or a vasodilator; wherein the support member includes a proximal end and a distal end, and a valve at the proximal end to prevent the inhalation of air mucus, and allow for the exhalation of air.

In another aspect, the present disclosure is directed to a method for treating lungs. The method may include coupling a first airway and a second airway through an exterior of the lungs to increase the forced expiratory volume of the lungs.

In yet another aspect, the present disclosure is directed to a method for treating a lung. The method may include forming a plurality of channels from an airway and through emphysematous alveoli disposed adjacent the airway, and inserting a support member through each of the plurality of channels.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or like parts or components. The term "distal" refers to the direction that is away from the user or operator and into the patient's body. By contrast, the term "proximal" refers to the direction that is closer to the user or operator and away from the patient's body.

Figure 1:
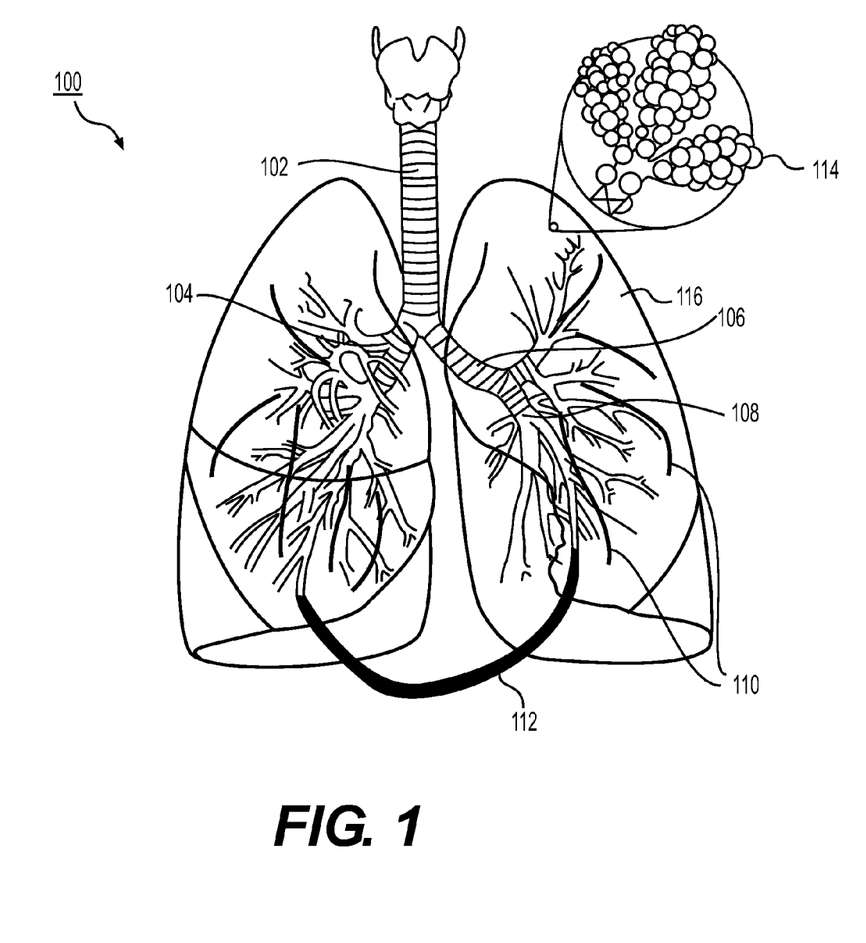
FIG. 1 illustrates an exemplary lung system having a plurality of collateral channels.

FIG. 1 illustrates a lung system 100 including a trachea 102. As air flows in through the nose and mouth, trachea 102 delivers the air to the lungs for respiratory functions. Trachea 102 divides into two main bronchi—the right primary bronchus 104 and the left primary bronchus 106. In lung system 100, both the right primary bronchus 104 and the left primary bronchus 106 divide into a plurality of bronchi, which further divide into a plurality of smaller airways, including airways 108. Airways 108 may be bronchi, bronchioles, or other suitable airways. Airways 108 may terminate into a plurality of alveoli 114 located in lung parenchyma 116. The alveoli 114 are small elastic air sacs which enable gas exchange between the pulmonary system and the circulatory system, including oxygen and $CO_2$ exchange.

During inhalation, air is delivered to the lungs and is received within the alveoli 114 via the respiratory airways. The inhaled air inflates the alveoli 114, allowing gaseous exchange with circulating blood to occur. Alveoli 114 subsequently recoil as air is exhaled. The normal operation of the lungs during inhalation and exhalation may be disturbed due to various lung conditions, e.g., emphysema.

Lung system 100 may be a damaged lung system exhibiting at least one symptom of COPD. In some embodiments, one or more airways 108 may be partially or completely blocked due to inflammation, excessive mucus production, among other factors. In some cases, the elastic recoil of alveoli 114 may be lost due to destruction of alveolar tissue. This destruction of tissue further causes a lack of support for small airways (tethering), which allows airways to collapse during exhalation, and as a result, inhaled air may not be completely expelled during exhalation. Thus, a patient's ability to exhale may be reduced, leading to $CO_2$ build-up in the alveoli 114 and/or airways 108.

As shown in FIG. 1, one or more channels 110 can be created within lung system 100 to improve collateral ventilation. The channels may be defined to include any opening, hole, slit, channel, or passage created within the lungs. In some embodiments, channels 110 may be formed between a healthy portion of the lung and a damaged portion of the lung, allowing air trapped in the damaged portion to be released through the healthy portion during exhalation. In some embodiments, the formation of channels 110 may increase the forced expiratory volume (FEV1) of the lungs. In some embodiments, channels 110 may extend through the parenchymal tissue of the lung to allow for fluid communication between two airways 108, or between an airway 108 and alveoli 114/parenchyma 116. In some embodiments, one of the airways 108 may be an obstructed airway and the other airway 108 may be a healthy airway. In some embodiments, a first airway 108 may be disposed in a first lobe such (e.g., an upper lobe) of the lung. In some embodiments, a second airway 108 may be disposed in a second lobe (e.g., a lower lobe) of the lung. In some embodiments, both airways 108 may be disposed in the same lobe of the lung.

A channel 112 may traverse outside the lung. That is, channel 112 may exit and re-enter an outer surface of the lung. In some embodiments, channel 112 may extend through the pleural cavity. By traversing through the pleural cavity, channels 112 may avoid unnecessary damage to healthy lung tissue. In some embodiments, channel 112 may form a link between the right lung and the left lung.

Additionally, channels 110 and 112 may be located at any suitable location within lung system 100. The number of channels depicted is exemplary, and any suitable number of channels can be formed within lung system 100 depending on the condition of the damaged lung system.

Channels 110, 112 may be formed between any two or more airways 108. Thus, channels 110, 112 may exit through the wall of one airway 108 and extend through lung parenchyma 116, connecting to at least one other airway 108. The channels 110, 112 may be formed using any suitable mechanism such as, e.g., cutting, RF ablation, laser ablation, or the like.

The diameters of the channels 110, 112 may be from about 0.25 mm up to about 10 mm, or may be another suitable diameter. In some embodiments, the diameters of channels 110, 112 may be from about 1 mm to about 4 mm. In some embodiments, channels 110, 112 may be formed of first, smaller diameter that is subsequently expanded to a second, larger diameter, after insertion of a support member into channels 110, 112.

For example, a channel 110, 112, having a first diameter of 1 mm may be formed through lung parenchyma 116. Then, a support member having an initial diameter slightly less than 1 mm in a collapsed configuration may be advanced through the channel 110, 112. After insertion into channel 110, 112, the support member may be moved to an expanded configuration having a second, larger diameter. Thus, after expansion of the support member, channels 110, 112 may be expanded to two times, three times, or to another suitable expansion of the first diameter. In such scenarios, a larger channel may be created without cutting or piercing a large portion of tissue. Thus, larger channels with a lower risk of closure due to mucus, inflammatory reactions, or other complications, may be formed with minimal damage to surrounding healthy tissue. Channels 110, 112 may have any suitable first and/or second diameters. In one embodiment, the diameter of channels 110, 112 may be between 0.25 mm and 10 mm.

In some embodiments, channels 110, 112 may couple two or more airways 108. For example, channels 110, 112, may extend from a first airway 108 to a second airway 108 while passing through various sections of the lung parenchyma 116 and additional airways 108.

In some embodiments, the channels 110, 112 may be treated or otherwise coated with an agent to inhibit tissue growth. Additionally, the cross-section of the channels 110, 112 may be circular, oval, rectangular, elliptical, or another suitable shape.

In some embodiments, the lungs may be imaged to facilitate channel selection and to identify healthy and diseased tissues. Alternatively, the identification of healthy and diseased tissues may be performed in any other suitable manner. In lungs having localized tissue damage, smaller lengths of channels 110, 112 may be used. In lungs having homogenous tissue damage, longer lengths of channels 110, 112 may be required.

Figure 2:
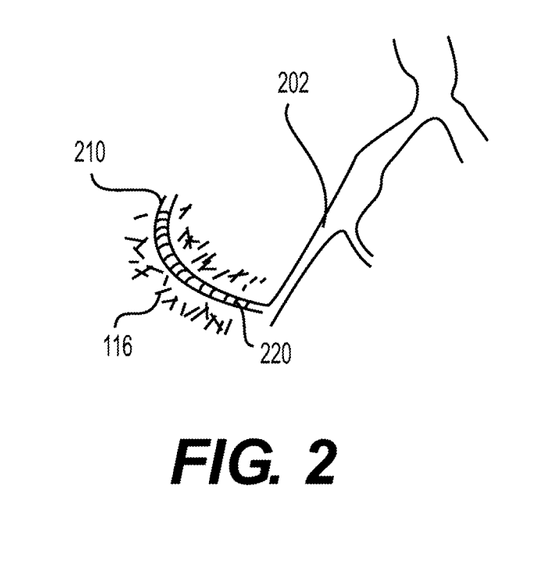
FIG. 2 illustrates a channel formed through the lung parenchyma in accordance with an embodiment of the present disclosure.

Referring to FIG. 2, a channel 210 may be formed between an airway 202 and lung parenchyma 116. Airway 202 may be substantially similar to airways 108 described with reference to FIG. 1. Channel 210 may be formed in a substantially similar manner as channels 110, 112 described with reference to FIG. 1. Once the channel 210 is formed, a support member 220 may be inserted through channel 210 to help prevent channel 210 from collapsing.

In some embodiments, lung parenchyma 116 may be diseased or otherwise damaged such that air remains trapped in lung parenchyma 116 after exhalation. Thus, the formation of channel 210 and the insertion of support member 220 may facilitate the release of the trapped air through a healthy airway 202. In other embodiments, lung parenchyma 116 may be relatively healthy, but may be prevented from expelling air due to an obstruction of an airway that normally couples lung parenchyma 116 to the respiratory pathways. In such embodiments, channel 210 and support member 220 may form a bypass between a healthy airway 202 and lung parenchyma 116.

In one embodiment, a channel 210 may be formed between a healthy airway 108 and healthy lung parenchyma 116, but may traverse through a portion of diseased parenchyma 116 in order to provide enhanced airflow through the diseased parenchyma 116.

Figure 3:
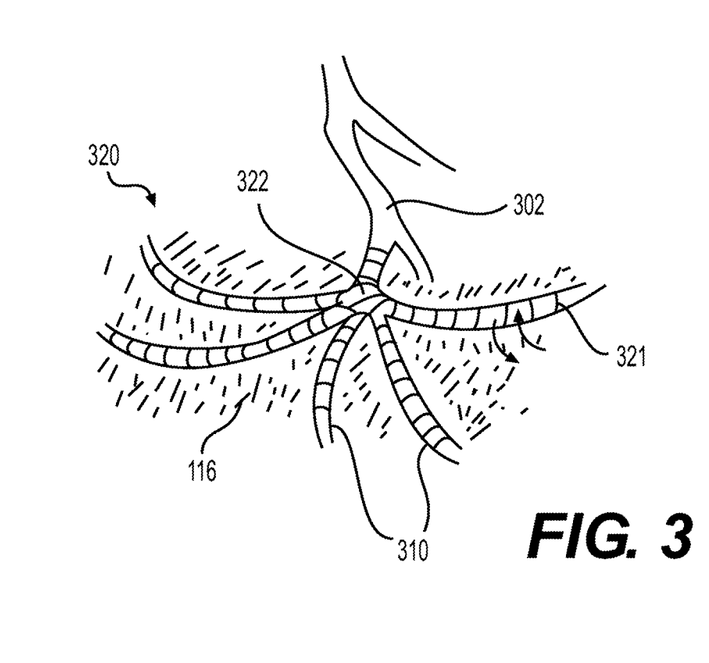
FIG. 3 illustrates a plurality of channels formed through the lung parenchyma in accordance with another embodiment of the present disclosure.

FIG. 3 shows a plurality of channels 310 formed between an airway 302 and lung parenchyma 116. A support member 320 may include a plurality of arms 321 that are disposed through the plurality of channels 310. Arms 321 may extend distally from a proximal branch point 322. In some embodiments, support member 320 may be movable from a collapsed configuration (not shown) where arms 321 are longitudinally constrained (e.g., by a sheath or other suitable elongate member) to an expanded configuration shown in FIG. 3. In the expanded configuration, arms 310 may extend radially outward from branch point 322 through lung parenchyma 116. In some embodiments, each channel 310 may be supported by an individual support member, such as, e.g., support member 220 described with reference to FIG. 2.

Channels 110, 112, 210, and 310 described herein may include one or more drainage ports configured to direct fluid from the channel toward the pleural cavity, lymph node or duct, abdominal cavity, bladder, or other suitable drainage location. The port may include a one-way valve that permits fluid flow from the channel toward a suitable drainage location, but not in the reverse direction. The drainage ports may help prevent the accumulation of fluid within the channels which may cause, e.g., blockages preventing proper functioning of the channels.

FIGS. 4-9 depict exemplary support members 400-900 that may be implanted into channels 110, 112, 210, and 310 (referring to FIGS. 1-3). In some embodiments, a given support member may extend through a part of, or through the entire length of a given channel. The support member may be elastic in an axial manner that pulls its proximal and distal ends together, increasing elasticity of the lung and aiding in the rapid exhalation of air. In some embodiments, the support member may be biased inward from its proximal and distal ends in order to bias the lung airways to exhale air. In some embodiments, the support member may be self-expandable, expandable by another suitable mechanism, or may be non-expandable.

In some embodiments, the support members 400-900 may be tapered at both the proximal and distal ends. In some embodiments, introduction members for introducing support members 400-900 may include an ultrasound sensor to identify presence of nerves and/or blood vessels during deployment.

The support members 400-900 may be generally circular in cross section. However, the support member members 400-900 may have other cross sectional shapes such as elliptical, polygonal, oblate, irregular, or the like. In additional embodiments, the support members 400-900 may have any cross-sectional configuration adapted to be received into a given channel.

The support members 400-900 may be formed from a resilient, flexible, and/or biocompatible material. Examples of such materials may include, but are not limited to, nitinol, silicone, polyurethane, HDPE, TEFLON, Dacron, stainless steel, metals, alloys, or the like. In some embodiments, the support members 400-900 may be formed from biodegradable materials including biodegradable polymers, or the like. Thus, in some embodiments, support members 400-900 may degrade over time, leaving the channel in place without the need for the support members 400-900. In some embodiments, the degradation may induce fibrosis in nearby tissue, which may facilitate in keeping the airway open.

The support members 400-900 may be coated with a substance (e.g., a drug) that helps prevent cell ingrowth into the channel. In some embodiments, support members 400-900 may include a pro-thrombotic to help prevent bleeding. In some embodiments, support members 400-900 may include a material to limit inflammatory reaction and cell growth that could block or otherwise obstruct a given channel. In some embodiments, support members 400-900 may include a time-releasable drug such as a bronchodilator, vasodilator, anti-restenosis drug, anti-stenotic drug, a drug preventing tissue ingrowth, a drug maintaining airway patency, an anti-inflammatory, or a mucolytic, among others. The bronchodilator may dilate the bronchioles to facilitate delivery of support members 400-900 or other devices through the channels. In some embodiments, these materials may include internal and/or external layers of lubricious material(s) in order to facilitate easy insertion of the support members 400-900 into an airway or channel.

In some embodiments, support members 400-900 may include a valve at a proximal end to prevent the inhalation of mucus. The valve may prevent mucus that could block or otherwise obstruct a given channel from being trapped within support members 400-900 or the channel. The valve may be a one-way valve that allows for the exhalation of trapped gases, but not the inhalation of air.

Figure 4:
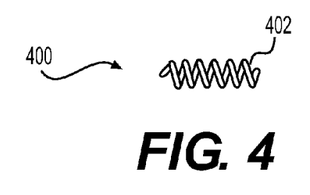
FIG. 4 illustrates a support member in a collapsed configuration in accordance with an embodiment of the present disclosure.
Figure 4A:
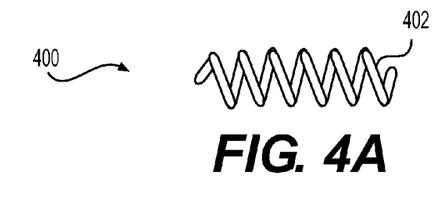
FIG. 4A illustrates the support member of FIG. 4 in an expanded configuration.

FIG. 4 shows a support member 400 in a collapsed configuration. Support member 400 may be an elongate member 402 formed as a spiral or coil. The support member 400 may be delivered into a newly-formed channel using an introduction device, or may be inserted into a previously-formed channel via a separate procedure. The introduction device may be a bronchoscope or another suitable introduction device.

In some embodiments, support member 400 may be inserted into a channel while in the collapsed configuration shown in FIG. 4. Support member 400 may subsequently be moved to an expanded configuration shown in FIG. 4A after insertion into the channel. In an alternative embodiment, support member 400 may be inserted into a channel while in the expanded configuration. Support member 400 may prevent tissue collapse while allowing air and liquid to pass through the airway lumen and between the coils of the support member 400. In particular, support member 400 may be suitable for applications requiring significant air throughput (e.g., in an airway or other area having significant bula or voids).

Figure 5:
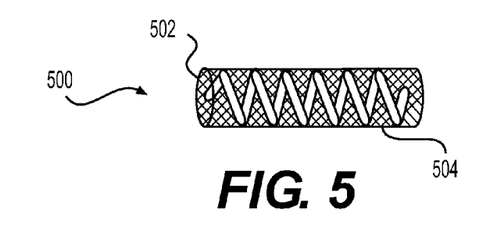
FIGS. 5-9 illustrate support members, in accordance with various embodiments of the disclosure.

A support member 500 is depicted in FIG. 5. Support member 500 may be an elongate member 502. Thus, support member 500 may be substantially similar to support member 400 except that support member 500 may include an outer member 504 that partially or completely covers elongate member 502. The outer member 504 may be a semi-permeable membrane that permits gaseous exchange. In some embodiments, outer member 504 may be impermeable to liquids. In one embodiment, the outer member 504 may be biodegradable. This may allow outer member 504 to help prevent tissue ingrowth after initial insertion into the airways, and when the risk of tissue ingrowth has subsided after a period of time, outer member 504 may degrade, leaving support member 500 to support the airway while simultaneously improving airflow.

In some embodiments, outer member 504 may form a unitary structure with the support member 500. In other embodiments, the outer member 504 may be assembled over the support member 500 before insertion into the patient. The outer member 504 may include any suitable flexible and/or biocompatible material, including, but not limited to, polymers, alloys, or the like. In some embodiments, the material may include polytetrafluoroethylene (PTFE), ethylene tetrafluoroethylene (ETFE), polyethylene terephthalate (PET), perfluoroalkoxy (PFA), polyether ether ketone (PEEK), polypropylene (PP), silicone, polycarbonate, polyurethane, LDPE, HDPE or the like.

Figure 6:
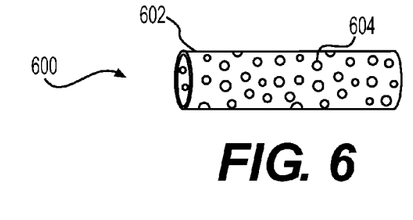

A support member 600 is depicted in FIG. 6. The support member 600 may be an elongate member 602 having a tubular shape or another suitable shape. The elongate member 602 may define a lumen extending between a proximal end and distal end. The support member 600 may include a plurality of pores 604 along the entire length of the support member 600. Alternatively, the pores 604 may be disposed partially along the length of the support member 600. Support member 600 may maintain airway patency and prevent debris from entering the channel defined by support member 600. In one embodiment, pores 604 may have a diameter of 10 microns or less, and may reduce cell proliferation while allowing air and liquid to pass through. Pores 604 may also have another suitable diameter. Support member 604 may be particularly useful in applications through the parenchyma having poor airflow and/or collateral airflow.

Figure 7:
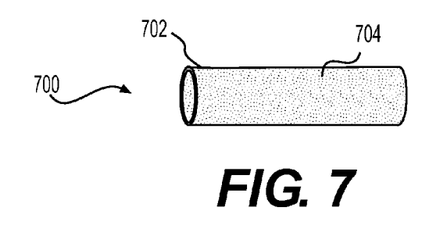

A support member 700 is depicted in FIG. 7. Support member 700 may be an elongate member 702 having a tubular shape or another suitable shape. Support member 700 may be substantially similar to support member 600 described with reference to FIG. 6 except that support member 700 may include pores 704 that are smaller than pores 604. Pores 704 may be disposed over a partial or entire surface of the support member 700. Pores 704 may permit gas exchange, while being impermeable to liquids. Support member 700 may be formed from one or more of Goretex, SIBS, latex, silicone, polyurethane, polytetrafluoroethylene (PTFE), ethylene tetrafluoroethylene (ETFE), perfluoroalkoxy (PFA), polyether ether ketone (PEEK), high density polyethylene (HDPE), polypropylene (PP), various copolymers, a scaffold material (e.g., collagen), decellurarized pericardium or other tissue (e.g., material similar to heart valve implants), or the like. In one embodiment, pores 704 may be smaller than 1 micron, or may have another suitable diameter. In one embodiment, support member 700 may be utilized when very little closure due to cell growth or liquid-filling is required. Support member 700 may be particularly useful when passing through parenchyma having good airflow characteristics.

Figure 8:
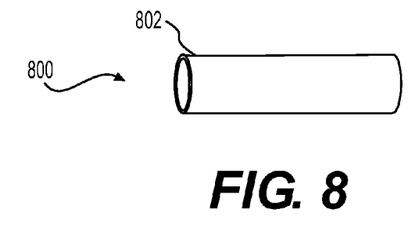

A support member 800 is depicted in FIG. 8. Support member 800 may be an elongate member 802 having a solid, tubular structure to provide sufficient support to a channel. In some embodiments, support member 800 may be impermeable to both liquids and gases. Support member 800 may be particularly useful in applications traversing the outside of the lung.

Figure 9:
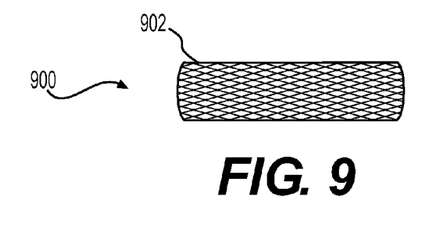

A support member 900 is depicted in FIG. 9 that is substantially similar to support member 400 described with reference to FIG. 4, except that support member 900 may include an elongate member 902 having a stent-shaped structure.

In some embodiments, the support members 400-900 may be self-expanding or may expand by another suitable mechanism after insertion into a channel, enlarging the channel after it has been deployed. For example, the support members 400-900 may be constrained in a collapsed configuration, for example by an outer sheath, until placed in the channel. The outer sheath may be subsequently removed to allow the respective support member 400-900 to expand to an expanded configuration.

Figure 10:
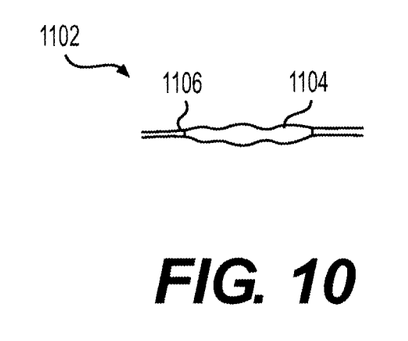
FIGS. 10 and 11 depict a mechanism for delivering an exemplary support member.
Figure 11:
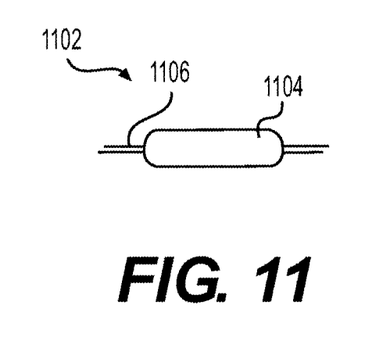

In other embodiments, the support members 400-900 may be expanded using an inflatable or expandable member such as balloon, stent, basket, push member, push-pull wire, or another suitable member. FIGS. 10 and 11 show an exemplary delivery member 1102 having an expandable member 1104 disposed over a guidewire 1106. In an alternative embodiment, expandable member 1104 may be disposed at the distal end of an elongate member. The expandable member 1104 may facilitate expansion of a support member 400-900 (referring to FIGS. 4-9). The support member 400-900 may be placed over expandable member 1104 while expandable member 1104 is in a collapsed configuration shown in FIG. 10. After delivery member 1102 and a given support member 400-900 are directed to a desired location, delivery member 1102 may be inflated or otherwise expanded to move a given support member 400-900 into an expanded configuration shown in FIG. 11. When expandable member 1104 is a balloon, it may be radially expanded using a fluid (e.g., gas or liquid) pressure to expand and deploy the support member 400-900. In other embodiments, the expandable member 1104 may be another suitable structure capable of expanding the support member 400-900, such as, e.g., a pull wire, push tube, guidewire, or the like.

Figure 12:
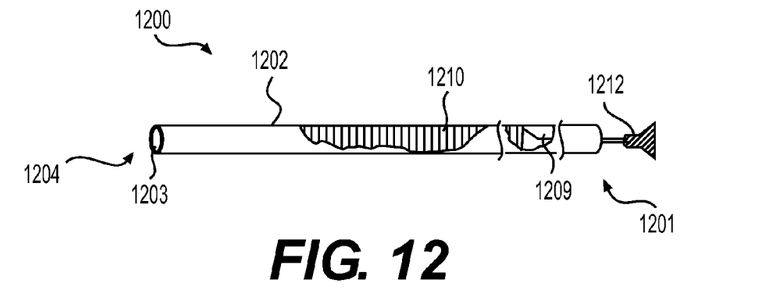
FIGS. 12-15 illustrate exemplary delivery devices, according to various embodiments of the present disclosure.

FIGS. 12-15 show various exemplary delivery mechanisms for delivering a support member into a channel. FIG. 12 shows a delivery device 1200 including an elongate member 1202. The elongate member 1202 may be a catheter or another suitable elongate member. In the embodiment of FIG. 12, an open-lumen catheter is shown. The elongate member 1202 may include a proximal end 1201, a distal end 1204, and a lumen 1209 extending between proximal end 1201 and distal end 1204. In some embodiments, the lumen 1209 may extend the entire length of the elongate member 1202, or alternatively, the lumen 1209 may extend through only a portion of the elongate member 1202. The distal end 1204 may include an opening 1203 and may be sufficiently sharp to penetrate through tissue to create one or more channels. The distal end 1204 may be circular or another suitable shape. A support member 1210 may be coupled to the distal end of an actuator 1212. In some embodiments, actuator 1212 may include a handle and a push rod that are slidable along a longitudinal axis of delivery device 1200. The support member 1210 may be substantially similar to any other support member described in the present disclosure.

In some embodiments, delivering a support member 1210 to a channel may include advancing the elongate member 1202 through the trachea and airways to a target location. Then, the elongate member 1202 may pierce through an airway wall to create a channel. Once the channel is created, the support member 1210 may be advanced through the elongate member 1202 using actuator 1212. Elongate member 1202 then may be withdrawn while leaving the support member 1210 in the channel. In some embodiments, delivery device 1200 may be disposed over a guidewire (not shown in FIG. 12).

Figure 13:
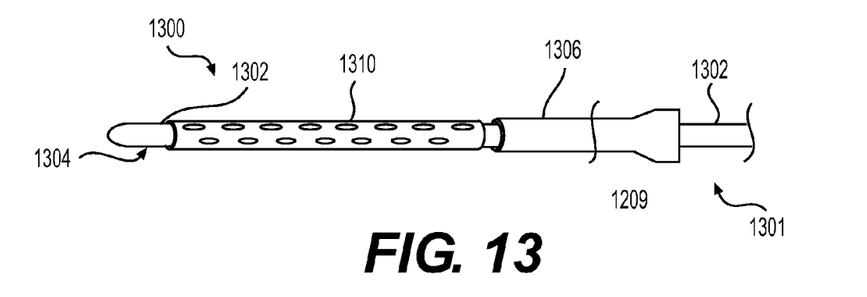

FIG. 13 shows a delivery device 1300 having an elongate member 1302. Elongate member 1302 may be a rod or another suitable elongate member. The elongate member 1302 may have a proximal end 1301 and a distal end 1304. The distal end 1304 may be sufficiently sharp to pierce through tissue. Along an outer surface of the elongate member 1302, a support member 1310 and an actuator 1306 may be disposed around elongate member 1302. In some embodiments, support member 1310 may be disposed distal to the actuator 1306. Actuator 1306 may be slidable along a longitudinal axis of delivery device 1300 to push the support member 1310 into a given channel when the elongate member 1302 reaches a target location. Support member 1310 may be substantially similar to any other support member described in the present disclosure.

In some embodiments, delivering the support member 1310 may include advancing the elongate member 1302 through the trachea and airways to a target location. Then, the elongate member 1302 may pierce through an airway wall to create one or more channels. The support member 1310 may be displaced from the outer surface of the elongate member 1302 by actuator 1306 to deliver support member 1310 to the channel. Then, the elongate member 1302 may be withdrawn leaving the support member 1310 in the channel.

Figure 14:
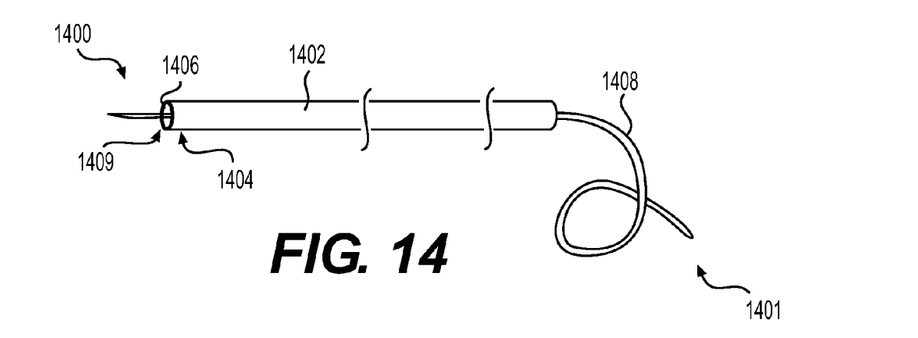

A delivery device 1400 is depicted in FIG. 14. Delivery device 1400 may have an elongate member 1402. The elongate member 1402 may have a proximal end 1401, a distal end 1404, and a lumen 1406 (e.g., a guidewire lumen) extending between the proximal end 1401 and the distal end 1404. The distal end 1404 may be sufficiently sharp to pierce through tissue. A guidewire 1408 may be passed through the lumen 1406 (or pre-loaded), and may be used for inserting a support member into a channel.

In some embodiments, delivering a support member may include advancing the elongate member 1402 through the trachea and airways to a target location. The elongate member 1402 may pierce through an airway wall to create one or more channels. Then, the guidewire 1408 may be advanced through the elongate member 1402 and then the elongate member 1402 may be withdrawn, leaving the guidewire 1408 in the channel. Then, a support member (not shown) may be advanced over the guidewire 1408 and through the channel. Finally, the guidewire 1408 may be removed leaving the support member in place.

Figure 15:
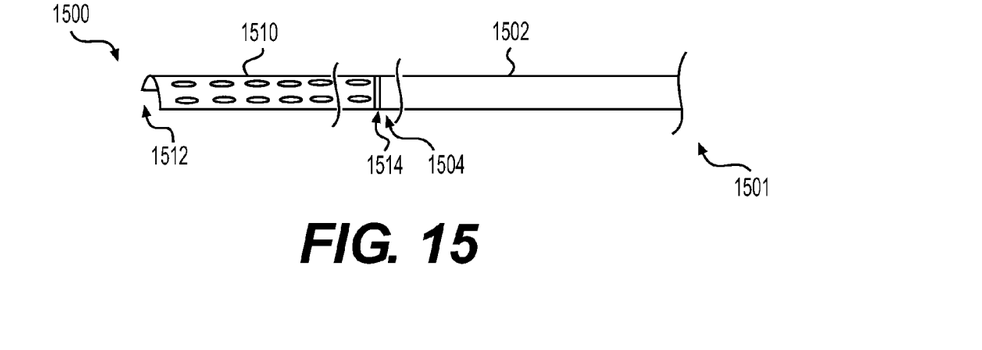

A delivery device 1500 is depicted in FIG. 15. Delivery device 1500 may have an elongate member 1502. The elongate member 1502 may have a proximal end 1501 and a distal end 1504. At the distal end 1504, a support member 1510 may be engaged or coupled with the elongate member 1502 using any suitable mechanism. In some embodiments, the distal end of support member 1510 may be sufficiently sharp to pierce through tissue. Once the elongate member 1502 reaches a target location, the support member 1510 may be disengaged at a link 1514. That is, link 1514 may be a frangible link coupling distal end 1504 of elongate member 1502 to a proximal end of support member 1510. Link 1514 may be severed by any suitable mechanism to displace the support member 1510 within the channel. Support member 1510 may be substantially similar to any other support member described in the present disclosure.

In some embodiments, a chronic total occlusion (CTO) bypass catheter, such as those used in coronary arteries, may be used for penetrating tissue and forming one or more channels.

Figure 16:
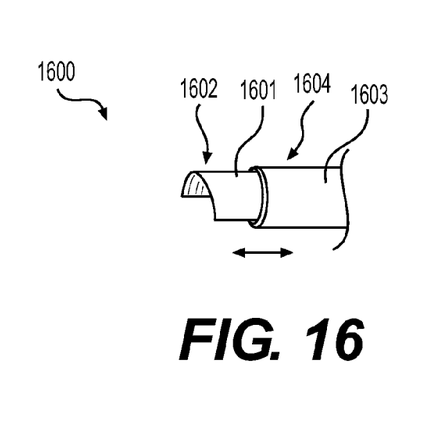
FIGS. 16-20 illustrate various mechanisms for creating channels within the lung system.

A delivery device 1600 is shown in FIG. 16. Delivery device 1600 may include an inner member 1601 having a distal end 1602, and an outer member 1603 having a distal end 1604. Inner member 1601 and outer member 1603 may be longitudinally displaceable relative to one another. Inner member 1602 may be disposed through a lumen of outer member 1603, and may also extend distal to distal end 1604 of outer member 1603 for piercing through tissue.

As shown in FIG. 16, the distal end 1602 of inner member 1601 may be bevelled or otherwise sufficiently sharp to pierce tissue and create one or more channels within the lung. In some embodiments, inner member 1602 may be a needle, cannula, blade, tube, rod, or other suitable tip. Distal end 1602 of inner member 1601 may be formed in any suitable shape, such as, e.g., curved, cone, circular, semi-circular, or the like. To pierce tissue, the distal end 1602 of inner member 1601 may be extended distal to distal end 1604 of outer member 1603, as shown in FIG. 16. When navigating delivery device 1600 at other times, the distal end 1602 of inner member 1601 may be retracted to be proximal to distal end 1604 of outer member 1603 to help avoid inadvertent tissue disruption or perforation. In one embodiment, inner member 1601 may be rotatable to facilitate boring or drilling of tissue.

In some embodiments, inner member 1601 and outer member 1603 may be coupled together using various coupling mechanisms as known in the art, and may both be formed from any suitable biocompatible material including one or more of metals, alloys, polymers, or the like. Inner member 1601 and outer member 1603 may be formed from the same material, or from different materials. In some embodiments, the inner member 1601 and outer member 1603 may be coated with a suitable low-friction material, such as polytetrafluoroethylene (PTFE), such as TEFLON®, polyetheretherketone (PEEK), polyimide, nylon, polyethylene, or other lubricious polymer coatings to reduce friction and subsequent trauma to tissues of the lung.

Figure 17:
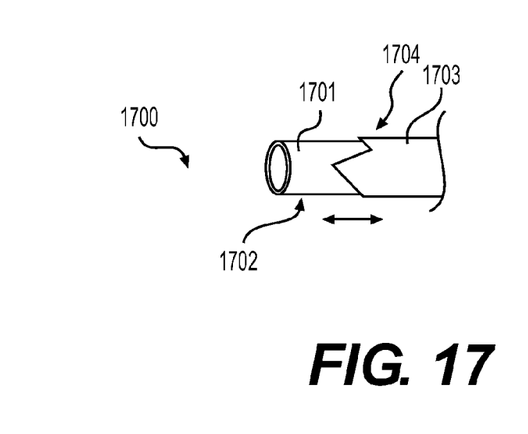

A delivery device 1700 is shown in FIG. 17. Delivery device 1700 may include an inner member 1701 having a distal end 1702, and an outer member 1703 having a distal end 1704. Inner member 1701 and outer member 1703 may be longitudinally displaceable relative to one another. Inner member 1702 may be disposed through a lumen of outer member 1703. Distal end 1704 of outer member 1703 may extend distal to distal end 1702 of inner member 1701 for piercing through tissue.

The distal end 1704 of outer member 1703 may be bevelled or otherwise sufficiently sharp to pierce tissue and create one or more channels within the lung. In some embodiments, outer member 1703 may be a needle, cannula, blade, tube, rod, or other suitable tip. Distal end 1704 of outer member 1703 may be formed in any suitable shape, such as, e.g., curved, cone, circular, semi-circular, or the like. To pierce tissue, the distal end 1704 of outer member 1703 may be extended distal to distal end 1702 of inner member 1701, as shown in FIG. 17. When navigating delivery device 1700 at other times, the distal end 1704 of outer member 1703 may be retracted to be proximal to distal end 1702 of inner member 1701 to help avoid inadvertent tissue disruption or perforation. In one embodiment, outer member 1703 may be rotatable to facilitate boring or drilling of tissue.

Inner member 1701 and outer member 1703 may be coupled in a substantially similar manner and formed of the same materials as inner member 1601 and outer member 1603 described with reference to FIG. 16.

Figures 18, 19:
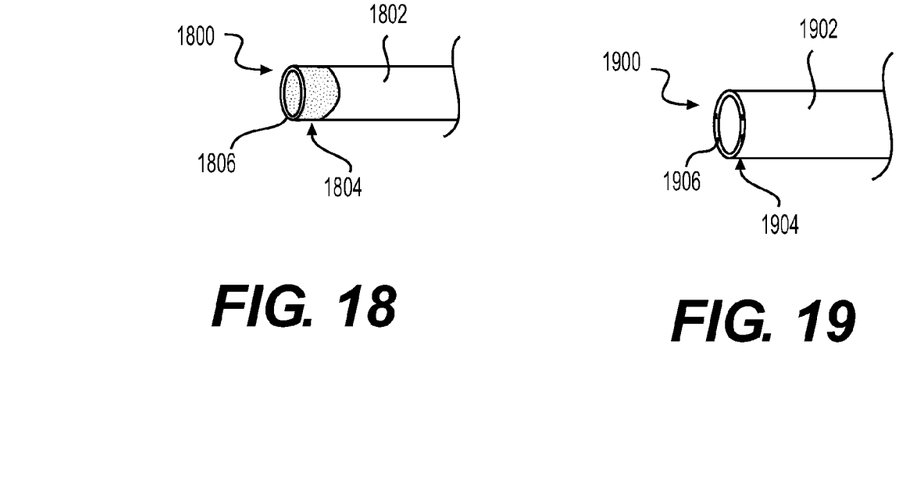

A delivery device 1800 is shown in FIG. 18. The delivery device 1800 may include an elongate member 1802 having a proximal end (not shown) and a distal end 1804. The distal end 1804 may include a tip 1806 such as a Radio Frequency (RF) electrode or an electro-cautery element, while the proximal end may be coupled to a suitable energy source (not shown). Thus, in some embodiments, RF energy may be transmitted from the energy source to tip 1806 such that the transmitted RF energy ablates or otherwise destroys tissue to create a channel through an airway wall and the lung parenchyma.

A delivery device 1900 is shown in FIG. 19. The delivery device 1900 may include an elongate member 1902 having a proximal end (not shown) and a distal end 1904. The distal end 1904 may include fibers 1906 that are configured to deliver laser energy. Laser energy may be delivered via fibers 1906 to ablate or destroy tissue to create a channel through an airway wall and the lung parenchyma.

Figure 20:
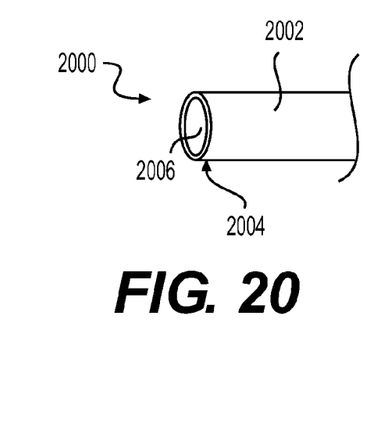

A delivery device 2000 is shown in FIG. 20. The delivery device 2000 may include an elongate member 2002 having a proximal end (not shown), a distal end 2004, and a lumen 2006 extending between the proximal end and distal end 2004. Argon gas or another suitable gas may be passed through the lumen 2006, delivering a focused stream of plasma that helps coagulate and seal the parenchymal or lung tissue. Thus, in some embodiments, delivery device 2000 may be an Argon plasma device utilized in bronchoscopic procedures.

Any of delivery devices 1800-2000 may also be rotated to facilitate tissue piercing and/or navigated over a guidewire or through a delivery sheath.

In some embodiments, the support members of the present disclosure may be coated with one or more the following therapeutic agents. Exemplary therapeutic agents that may help prevent excessive cell growth may include Paclitaxel, and various olimus drugs (everolimus, sirolimus). The term "therapeutic agent" as used in the present disclosure may encompass therapeutic agents, genetic materials, and biological materials and can be used interchangeably with "biologically active material". In one embodiment, the therapeutic agent may be an anti-cell proliferation (restenotic) agent. In other embodiments, the therapeutic agent may inhibit smooth muscle, contraction, migration or hyperactivity, mucus production and mucus thickening. Non-limiting examples of suitable therapeutic agent may include heparin, heparin derivatives, clotting or haemostatic agents to stem acute bleeding from device implantation urokinase, dextrophenylalanine proline arginine chloromethylketone (PPack), enoxaprin, angiopeptin, hirudin, acetylsalicylic acid, tacrolimus, everolimus, zotarolimus, rapamycin (sirolimus), pimecrolimus, zotarolimus, amlodipine, doxazosin, glucocorticoids, betamethasone, dexamethasone, prednisolone, corticosterone, budesonide, sulfasalazine, rosiglitazone, mycophenolic acid, mesalamine, paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, platelet receptor antagonists, antithrombin antibodies, anti-platelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, vasodilating agents, agents which interfere with endogenous vasoactive mechanisms, antioxidants, probucol, antibiotic agents, penicillin, cefoxitin, oxacillin, tobramycin, angiogenic substances, fibroblast growth factors, estrogen, estradiol (E2), estriol (E3), 17-beta estradiol, digoxin, beta blockers, captopril, enalopril, statins, steroids, vitamins (e.g., vitamin A may have lung repair properties), paclitaxel (as well as its derivatives, analogs or paclitaxel bound to proteins, e.g. Abraxane™) 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, 2'-O-ester with N-(dimethylaminoethyl) glutamide hydrochloride salt, nitroglycerin, nitrous oxides, nitric oxides, antibiotics, aspirins, digitalis, estrogen, estradiol and glycosides. In one embodiment, the therapeutic agent may be a smooth muscle cell inhibitor or antibiotic. In one embodiment, the therapeutic agent may be taxol (e.g., Taxol®), or its analogs or derivatives. In another embodiment, the therapeutic agent may be paclitaxel, (i.e. paclitaxel, its analogs or derivatives). In yet another embodiment, the therapeutic agent may be an antibiotic such as erythromycin, amphotericin, rapamycin, adriamycin, or the like.

Genetic materials may include DNA or RNA, including, such as, e.g., DNA/RNA encoding a useful protein stated below, intended to be inserted into a human body, including viral vectors and non-viral vectors.

Biological materials may include cells, yeasts, bacteria, proteins, peptides, cytokines and hormones. Examples of peptides and proteins may include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (EGGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. In some embodiments, BMP's may be BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells may include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other non-genetic therapeutic agents may include: anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, acetylsalicylic acid, tacrolimus, everolimus, amlodipine and doxazosin; anti-inflammatory agents such as glucocorticoids, betamethasone, dexamethasone, prednisolone, corticosterone, budesonide, estrogen, sulfasalazine, rosiglitazone, mycophenolic acid and mesalamine; anti-neoplastic/anti-proliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, cladribine, taxol and its analogs or derivatives; anesthetic agents such as lidocaine, bupivacaine, and ropivacaine; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory therapeutic agent), dipyridamole, protamine, hirudin, prostaglandin inhibitors, platelet inhibitors, antiplatelet agents such as trapidil or liprostin and tick antiplatelet peptides; DNA demethylating therapeutic agents such as 5-azacytidine, which is also categorized as a RNA or DNA metabolite that inhibit cell growth and induce apoptosis in certain cancer cells; vascular cell growth promoters such as growth factors, vascular endothelial growth factors (VEGF, all types including VEGF-2), growth factor receptors, transcriptional activators, and translational promoters; vascular cell growth inhibitors such as anti-proliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents, vasodilating agents, and agents which interfere with endogenous vasoactive mechanisms; anti-oxidants, such as probucol; antibiotic agents, such as penicillin, cefoxitin, oxacillin, tobranycin, rapamycin (sirolimus); angiogenic substances, such as acidic and basic fibroblast growth factors, estrogen including estradiol (E2), estriol (E3) and 17-beta estradiol; therapeutic agents for heart failure, such as digoxin, beta-blockers, angiotensin-converting enzyme (ACE) inhibitors including captopril and enalopril, statins and related compounds; and macrolides such as sirolimus, everolimus, tacrolimus, pimecrolimus or zotarolimus.

Biological materials may include anti-proliferative therapeutic agents such as steroids, vitamins, and restenosis-inhibiting agents. In some embodiments, restenosis-inhibiting agents may include microtubule stabilizing agents such as Taxol®, paclitaxel (i.e., paclitaxel, paclitaxel analogs, or paclitaxel derivatives, and mixtures thereof). For example, derivatives suitable for use in the present disclosure may include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other suitable therapeutic agents may include tacrolimus; halofuginone; inhibitors of HSP90 heat shock proteins such as geldanamycin; microtubule stabilizing agents such as epothilone D; phosphodiesterase inhibitors such as cliostazole; Barkct inhibitors; phospholamban inhibitors; and Serca 2 gene/proteins.

Other suitable therapeutic agents may include nitroglycerin, nitrous oxides, nitric oxides, aspirins, digitalis, estrogen derivatives such as estradiol and glycosides.

In some embodiments, the therapeutic agent may be capable of altering the cellular metabolism or inhibiting a cell activity, such as protein synthesis, DNA synthesis, spindle fiber formation, cellular proliferation, cell migration, microtubule formation, microfilament formation, extracellular matrix synthesis, extracellular matrix secretion, or increase in cell volume. In other embodiments, the therapeutic agent may be capable of inhibiting cell proliferation and/or migration.

In certain embodiments, the therapeutic agents for use in the medical devices of the present disclosure can be synthesized by methods well known to one skilled in the art.

In some embodiments, the devices disclosed in the present disclosure can be employed along with an elongate member such as a catheter that functions as a lumen or channel to introduce and deliver the disclosed devices to a target site within a patient's body. The devices also may be used along with other introduction devices, sheaths, or systems, such as bronchoscopes, trocars, endoscopes, endoscopic system, laparoscopes, colonoscopes, ureterscope, or the like.

In some embodiments, support members of the present disclosure may include one or more fixation members for securing the support member within, e.g., a void. For example, the support members may include a single balloon, double balloon, or flange, to secure the support member to an airway wall or within a void. Examples of fixation members include, but are not limited to, fixation members used in patent foramen ovale devices.

Although the exemplary embodiments described above have been disclosed in connection with medical devices for insertion into a lung system for effective expelling of the air from the lung, those skilled in the art will understand that the principles set out above can be applied to any bronchial device and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Other exemplary embodiments of the present disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the present disclosure as defined by the following claims.

What is claimed is:

1. A method for treating a lung, the method comprising:
   forming a channel between a first airway and a second airway through a tissue of the lung to allow air trapped within the first airway to flow through the channel and the second airway; and
   inserting a support member into the channel, wherein an entirety of the support member is biodegradable, and the support member includes an outer member that is permeable to gases and impermeable to liquids.

2. The method of claim 1, wherein the tissue of the lung includes parenchymal tissue of the lung.

3. The method of claim 1, wherein the channel extends through a third airway.

4. The method of claim 1, wherein the tissue of the lung includes alveoli.

5. The method of claim 1, wherein the support member is a spiral member.

6. The method of claim 1, wherein the support member is inserted via a bronchoscopic member, the support member remains in the channel after the bronchoscopic member has been removed from the lung, the support member is coupled to the distal end of the bronchoscopic member by a frangible link, and the frangible link is severed to secure the support member within the channel.

7. The method of claim 1, wherein the support member includes:
   a proximal end and a distal end; and
   a valve at the proximal end to prevent inhalation of air mucus, and allow for exhalation of air.

8. The method of claim 1, wherein, after degradation of the support member, the channel is defined only by the tissue of the lung.

9. The method of claim 8, wherein the support member includes a biodegradable polymer.

10. The method of claim 1, wherein the outer membrane is configured to degrade before a remainder of the support member degrades.

11. The method of claim 10, wherein the support member is a spiral member that coils around a central lumen.

12. The method of claim 11, wherein the support member further includes a bronchodilator.

13. A method for treating lungs, the method comprising:
   coupling a first airway in a left lung of a patient and a second airway in a right lung of the patient, or coupling a first lung lobe of the patient and a second lung lobe of the patient, through a support member that extends through a pleural cavity of the patient to increase a forced expiratory volume of the lungs, wherein a first end of the support member is inserted into the left lung, and a second end of the support member is inserted into the right lung, or the first end of the support member is inserted into the first lung lobe and the second end of the support member is inserted into the second lung lobe.

14. The method of claim 13, wherein at least a portion of the support member is biodegradable and includes a biodegradable polymer.

15. A method for treating a lung, the method comprising:
   forming a plurality of channels from an airway and through emphysematous alveoli disposed adjacent the airway; and
   inserting a support member into the lung, the support member including a branch point and at least three arms each extending radially outward from the branch point, wherein each of the plurality of channels receives one of the at least three arms, the support member further includes a biodegradable polymer, and an outer member that is permeable to gases and impermeable to liquids, and after degradation of the support member, each of the plurality of channels is defined only by the tissue of the lung.

16. The method of claim 15, wherein an entirety of the support member is biodegradable.

\* \* \* \* \*